(12) United States Patent
Alasaarela (10) Patent No.: US 8,890,871 B2
(45) Date of Patent: Nov. 18, 2014

(54) METHOD AND ARRANGEMENT FOR MONITORING THE PATH OF AN ANIMAL OR A HUMAN IN THE HOME

(75) Inventor: Esko Alasaarela, Oulu (FI)

(73) Assignee: Domuset Oy, Oulu (FI)

( * ) Notice: Subject to any disclaimer, the term of this patent is extended or adjusted under 35 U.S.C. 154(b) by 116 days.

(21) Appl. No.: 13/503,608

(22) PCT Filed: Oct. 20, 2010

(86) PCT No.: PCT/FI2010/050824
§ 371 (c)(1),
(2), (4) Date: Apr. 23, 2012

(87) PCT Pub. No.: WO2011/055004
PCT Pub. Date: May 12, 2011

(65) Prior Publication Data
US 2012/0206454 A1    Aug. 16, 2012

(30) Foreign Application Priority Data

Nov. 6, 2009 (FI) .................................. 20096151

(51) Int. Cl.
*G06T 11/20* (2006.01)
*A01K 29/00* (2006.01)
*A01K 15/02* (2006.01)
*A61B 5/11* (2006.01)

(52) U.S. Cl.
CPC .............. *A01K 29/00* (2013.01); *A01K 15/021* (2013.01); *A61B 5/1113* (2013.01); *A61B 2562/0219* (2013.01)
USPC ....................................................... 345/440

(58) Field of Classification Search
CPC ........................................................ G06T 11/20
USPC ........... 345/440; 340/539.13, 539.14; 702/95, 702/94
See application file for complete search history.

(56) References Cited

U.S. PATENT DOCUMENTS 6,249,252 B1 *   6/2001   Dupray ........................ 342/450
6,377,211 B1 *   4/2002   Hsiung ........................ 342/359
(Continued)

FOREIGN PATENT DOCUMENTS

CN   101324662 A   12/2008
JP   2007299121 A  11/2007
(Continued)

OTHER PUBLICATIONS

International Search Report for parent application PCT/FI2010/050824, having a mailing date of Feb. 23, 2011.

(Continued)

*Primary Examiner* — David Zarka
*Assistant Examiner* — Brian Kravitz
(74) *Attorney, Agent, or Firm* — Andrus Intellectual Property Law, LLP (57) ABSTRACT

A monitoring method of a path of an animal can be realized via a data transfer network, a monitoring arrangement used in the method, a server and a computer program to be used in the monitoring arrangement, which are included in the monitoring arrangement. With the method and monitoring arrangement, the path of a monitored living target can be visualized on a data processing device for a selected time period. The data processing device can be situated in a different location than the animal being monitored. The recent 3D acceleration measurement data of the living target is compared to the long-term average data. The measurement data used in determining the path are obtained from the wireless monitoring device, which the animal carries with it.

15 Claims, 6 Drawing Sheets

(56) References Cited

U.S. PATENT DOCUMENTS

| | | | |
|---|---|---|---|
| 6,487,992 B1 | 12/2002 | Hollis | |
| 6,856,863 B1* | 2/2005 | Sundar | 700/254 |
| 2002/0103610 A1 | 8/2002 | Bachmann et al. | |
| 2002/0175897 A1* | 11/2002 | Pelosi | 345/158 |
| 2002/0196151 A1 | 12/2002 | Troxler | |
| 2004/0021569 A1* | 2/2004 | Lepkofker et al. | 340/568.1 |
| 2004/0044493 A1* | 3/2004 | Coulthard | 702/122 |
| 2004/0174264 A1* | 9/2004 | Reisman et al. | 340/573.4 |
| 2005/0068169 A1* | 3/2005 | Copley et al. | 340/539.13 |
| 2005/0242947 A1* | 11/2005 | Burneske et al. | 340/539.13 |
| 2006/0011144 A1 | 1/2006 | Kates | |
| 2006/0267833 A1* | 11/2006 | Langford et al. | 342/174 |
| 2007/0188494 A1* | 8/2007 | Agutter et al. | 345/440 |
| 2007/0189510 A1* | 8/2007 | Tanaka et al. | 380/28 |
| 2007/0204804 A1 | 9/2007 | Swanson et al. | |
| 2007/0276270 A1* | 11/2007 | Tran | 600/508 |
| 2007/0295277 A1 | 12/2007 | Kin et al. | |
| 2008/0077326 A1* | 3/2008 | Funk et al. | 701/220 |
| 2008/0253225 A1* | 10/2008 | Welker et al. | 367/17 |
| 2009/0043504 A1* | 2/2009 | Bandyopadhyay et al. | 701/213 |
| 2009/0079830 A1* | 3/2009 | Ekpar | 348/148 |
| 2009/0090305 A1 | 4/2009 | Cheok et al. | |
| 2009/0111526 A1* | 4/2009 | Masri | 455/566 |
| 2009/0199114 A1* | 8/2009 | Lewis et al. | 715/763 |
| 2009/0201149 A1* | 8/2009 | Kaji | 340/539.13 |
| 2009/0210368 A1* | 8/2009 | Deo et al. | 706/20 |
| 2009/0314088 A1* | 12/2009 | Djordjevic et al. | 73/602 |

FOREIGN PATENT DOCUMENTS

| | | |
|---|---|---|
| WO | 2008/140992 A1 | 11/2008 |
| WO | 2009/105243 A2 | 8/2009 |

OTHER PUBLICATIONS

Venkatraman, S. et al, "Wireless Inertial Sensors for Monitoring Animal Behavior", Proceedings of the 29th Annual International Conference of the IEEE Engineering in Medicine and Biology Society, Lyon, France, Aug. 23-26, 2007; pp. 378-381.

Search Report for priority application FI 20096151, dated May 20, 2010.

* cited by examiner

METHOD AND ARRANGEMENT FOR MONITORING THE PATH OF AN ANIMAL OR A HUMAN IN THE HOME

CROSS-REFERENCE TO RELATED APPLICATIONS

This application is the U.S. national stage application of International Application No. PCT/FI2010/050824, filed Oct. 20, 2010, which International application was published on May 12, 2011 as International Publication No. WO 2011/055004 A1 in the English language and which application is incorporated herein by reference. The International application claims priority of Finnish Patent Application No. 20096151, filed Nov. 6, 2009, which application is incorporated herein by reference.

FIELD OF DISCLOSURE

The invention relates to a method for monitoring the path of a target, an animal or a human, within a defined area via a data transfer network. The invention also relates to a monitoring arrangement for the path of a target and a server utilized in the path monitoring arrangement and a computer program used in the monitoring of a path.

BACKGROUND

The aging part of the population grows quickly in industrialized countries. An aging person often lives in a place, where relatives or friends do not have time to visit sufficiently often in order to assess the health and ability of the person. In such a case the worry of the relatives and friends for how the person they are close to manages in their daily routines can become great.

In order to eliminate such a situation, various computerized solutions have been developed, by using which the daily activities of a person or several persons can be monitored on a rough level. The apartment, which a person uses, can for example be equipped with various door or room sensors, which indicate the use of the door or the movement of the person inside the room.

Thus the person's movement can be discovered over a certain time period. If no signals regarding the person's movement are received from the sensors either during a certain time or at certain time intervals, the arrangement provides an alarm, which is relayed through the data network. Examples of such monitoring systems are shown in the patents JP 2007299121 and CN 101324662.

Solutions are also known, wherein the person has a device for example on his or her wrist, which device can monitor vital functions or which can be used to send an alarm to an external person in situations, where the person feels that his or her ability has weakened. The alarm can be sent for example via radio, telephone or the internet.

Even though the description of this application concentrates mainly on monitoring the path of a pet staying in the home, the same problems and solutions can also be applied for monitoring the movements and activities of a human living at home.

Buying and caring for various pets continuously becomes more common. Caring for pets is an element, which counter-balances the rush for a busy human. The care of the pet however always takes up time from its owner. It is not in all situations possible, however, for the owner to be always with his pet or to control its behaviour.

If the owner needs to be away from the house every day for long periods of time, the life of the pet can become so boring that the pet develops various forms of destructive behaviour. Thus a place can for example be booked for the pet at a pet care facility or an external person can be employed to care for the pet daily during at least a part of the day.

Various pet monitoring and controlling means functioning via data networks are also known. Especially the emergence and development of the internet as a central communication channel has made the development of various pet monitoring and controlling systems easier. With such monitoring and controlling means the behaviour of a pet can be monitored in real-time either via video image or an audio dispatch also when outside the home. From the video images and/or the sounds of the pet one can deduce in what kind of activity state the pet is at that exact moment.

The movement and recreation of the pet can also be monitored in real-time via a data network. The positioning of the pet in the home can be realized for example with video surveillance, RFID identifier readers, GPS, infrared sensors, acoustic positioning methods, radio positioning or calculation of the position based on acceleration measurement.

The controlling of the operation of various food and drink dispensers used by the pets can also be managed via a data network. Such a food dispenser is known for example from application publication US 2007/0295277.

Training and/or play direction for a pet, which occurs through a data network, is also known. One such remote training system is presented in application publication WO 2008/140992.

It is also possible to realize physical handling or petting of a pet through a data network. Application publication US 2009/0090305 shows an arrangement, by means of which a petting device in the possession of the owner can provide a real sensation on the skin of the pet.

If the pet owner's life becomes so busy that he does not have time to monitor the activity of the pet via a data network in real-time, then it is possible to assign at least some part of the controlling of the daily activities of the pet to a suitably programmed home computer. In such a system a computer in the home simulates the owner during at least a part of the day. One such arrangement is depicted in application publication US 2006/0011144. The depicted arrangement comprises real-time positioning of a pet (dog) with various methods, control of the food and drink dispensers, monitoring of the activity state of the dog with an acceleration sensor (in its place or moving), monitoring of the body temperature of the dog, monitoring the barking of the dog, creating various scent, sound and picture animations depicting the owner and showing them to the dog. If an activity model, which differs from the normal, can be observed in the activity of the dog at a certain time, the computer sends an alarm regarding the matter to the pet owner. The solution shown in the reference publication can thus give an alarm, if the activity of the dog momentarily differs sufficiently from the activity models stored in the memory of the computer.

The arrangement shown in reference publication US 2006/0011144 cannot make conclusions in situations, where the activity of a dog surprisingly changes, even if the activity stays within normal limits, but the movement of the dog still changes either temporarily or little by little to differ completely from the normal movement. For example the dog moves as much as before, but the movement area has changed from the usual. In such cases a conclusion made by the pet owner, regarding what has caused the situation, would also be needed.

The same conclusion problem also applies to the movement of a human, for example an elderly human, living alone at home, which movement may reveal a change occurring in his or her state of health.

SUMMARY

It is an object of the invention to present an arrangement, which can utilize data obtained through long-term monitoring of a target in the monitoring and controlling of a living target, a human or an animal. With the aid of long-term monitoring such changes in behaviour in the target, which do not become apparent in short-term observations, can be discovered. Long-term monitoring can make use of for example characteristics of behaviour that are typical in different breeds of dogs or special characteristics caused by cultural differences in people.

The objects of the invention are obtained with a system, where temporary movement and behaviour data obtained by means of acceleration measurement and other sensors attached to a human or a pet are compared to long-term measurement data describing the behaviour and the state of the human or pet in order to discover a possible problem with the target.

It is an advantage of the invention that a change in the behaviour of the target, the human or the pet, becomes evident also in situations, where a temporary activity of the target does not indicate the existence of a problem.

It is a further advantage of the invention that in analyzing the problem, the movement of the human or pet in the apartment can be visualized to a relative or owner via a data network at time intervals selected by the user. In visualizing the movement the location of the target's rest place can be used as the initial data, a calibration data of sorts, when the target begins to move for example after resting.

It is a further advantage of the invention that all other activities discovered during the movement of the human or pet can be visualized at their occurrence locations.

It is a further advantage of the invention that all the changes detected in the activities of the pet can be used to conclude the approach of a natural disaster, which the pet can sense.

It is a further advantage of the invention that the movement of a human or pet in the apartment at a certain time can be visualized also to external observers. With the aid of this information the arrival of an external caretaker to perform treatments on the target can be timed.

The method according to the invention for presenting the path of a living target is characterized in that the method comprises
  performing calibration of the rest place of a living target
  correcting with the aid of the rest place data the measurement location and measurement direction data related to the short-term 3D acceleration measurement data starting from the latest rest place and
  sending corrected path data to at least one data processing device.

The monitoring arrangement of a target's path according to the invention is characterized in that the arrangement comprises
  means for determining and calibrating a target's rest place data
  means for correcting with the aid of the rest place data the measurement location and measurement direction data related to the short-term 3D acceleration measurement data starting from the target's latest rest place and
  means for sending corrected path data to at least one data processing device.

The server according to the invention, which is utilized in presenting the path of a living target, is characterized in that the server comprises
  means for determining and calibrating a target's rest place data
  means for correcting with the aid of the rest place data the measurement location and measurement direction data related to the short-term 3D acceleration measurement data starting from the target's latest rest place and
  means for sending corrected path data to at least one data processing device.

The computer program product according to the invention, which is utilized in evaluating the ability of a living target, is characterized in that it comprises computer code means stored in a computer readable storage means, which code means are arranged to
  perform calibration of the rest place of a target
  correct with the aid of the rest place data the measurement location and measurement direction data related to the short-term 3D acceleration measurement data starting from the latest rest place and
  send corrected path data to at least one data processing device.

Some advantageous embodiments of the invention are presented in the dependent claims.

The basic idea of the invention is the following: The living target to be monitored, a human or a pet, is equipped with a device, which is able to convey different information about the state and movement of the target via radio contact to a data processing device in the home. The device carried by the target advantageously comprises a processor unit and a thereto connected memory unit, a transmitter-receiver, at least one 3D acceleration measurement apparatus and a microphone. The device carried by the target can also comprise a compass, a gyro sensor, a thermometer, a device controlling the activity and rewarding of the target and a video camera.

When the target moves, the 3D acceleration sensor is used to calculate the position of the target after a specified time interval. Each position data is stored first in the memory unit of the device carried by the target. At times the position data is sent to a base station in the home. A conventional PC can for example function as the base station, whereto a suitable transmitter-receiver has been connected.

All the other measurement data describing the behaviour or the physical state of the target are also transferred to a PC in the home. Examples of such data are for example the rest place and rest time, sound-making time, body temperature, heart rate and feeding and drinking occurrences of the target.

From the PC in the home the obtained measurement data is advantageously transferred to a server on the internet. Via the server, monitoring data for the target can be presented to the target's relative or owner or another person or organization, to whom the target's relative or owner has granted access to view the target's monitoring data. With the aid of the data comprised in the server, data regarding the behaviour and state of the target can be presented to the relative or owner of the target, for a period of time determined by the relative or owner. By utilizing the long-term monitoring results contained in the server, slow changes occurring in the behaviour of the target can be discovered, which changes are not discovered from real-time monitoring data and the causes of which should be clarified by the relative or owner.

BRIEF DESCRIPTION OF THE DRAWINGS

In the following, the invention will be described in detail. In the description, reference is made to the appended drawings, in which.

DETAILED DISCLOSURE

The embodiments in the following description are given as examples only and someone skilled in the art can carry out the basic idea of the invention also in some other way than what is described in the description. Though the description can refer to a certain embodiment or embodiments in several places, this does not mean that the reference would be directed towards only one described embodiment or that the described characteristic would be usable only in one described embodiment. The individual characteristics of two or more embodiments can be combined and new embodiments of the invention can thus be provided.

Figure 1:
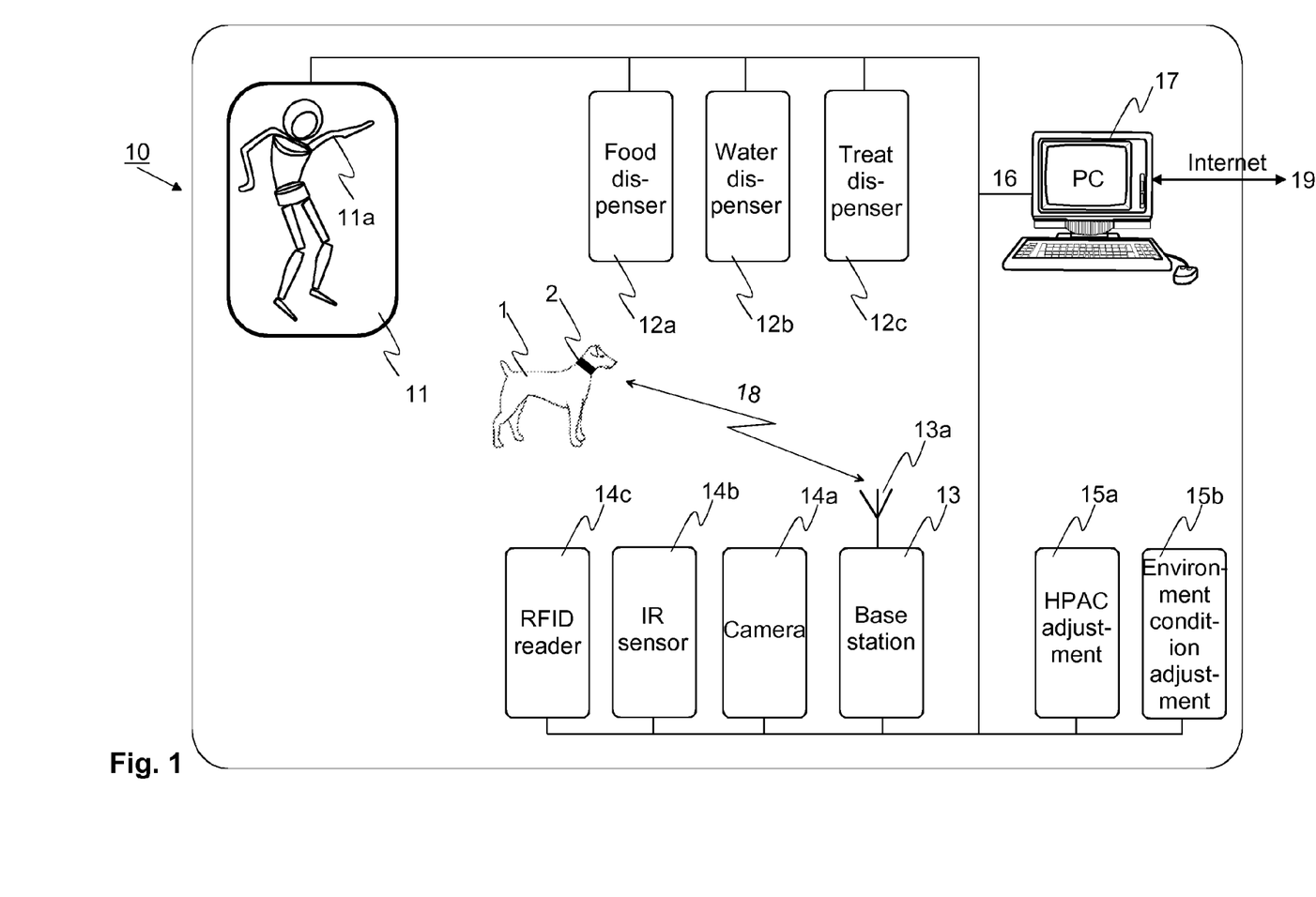
FIG. 1 shows a device arrangement for caring for a target according to an embodiment of the invention.
Figure 4:
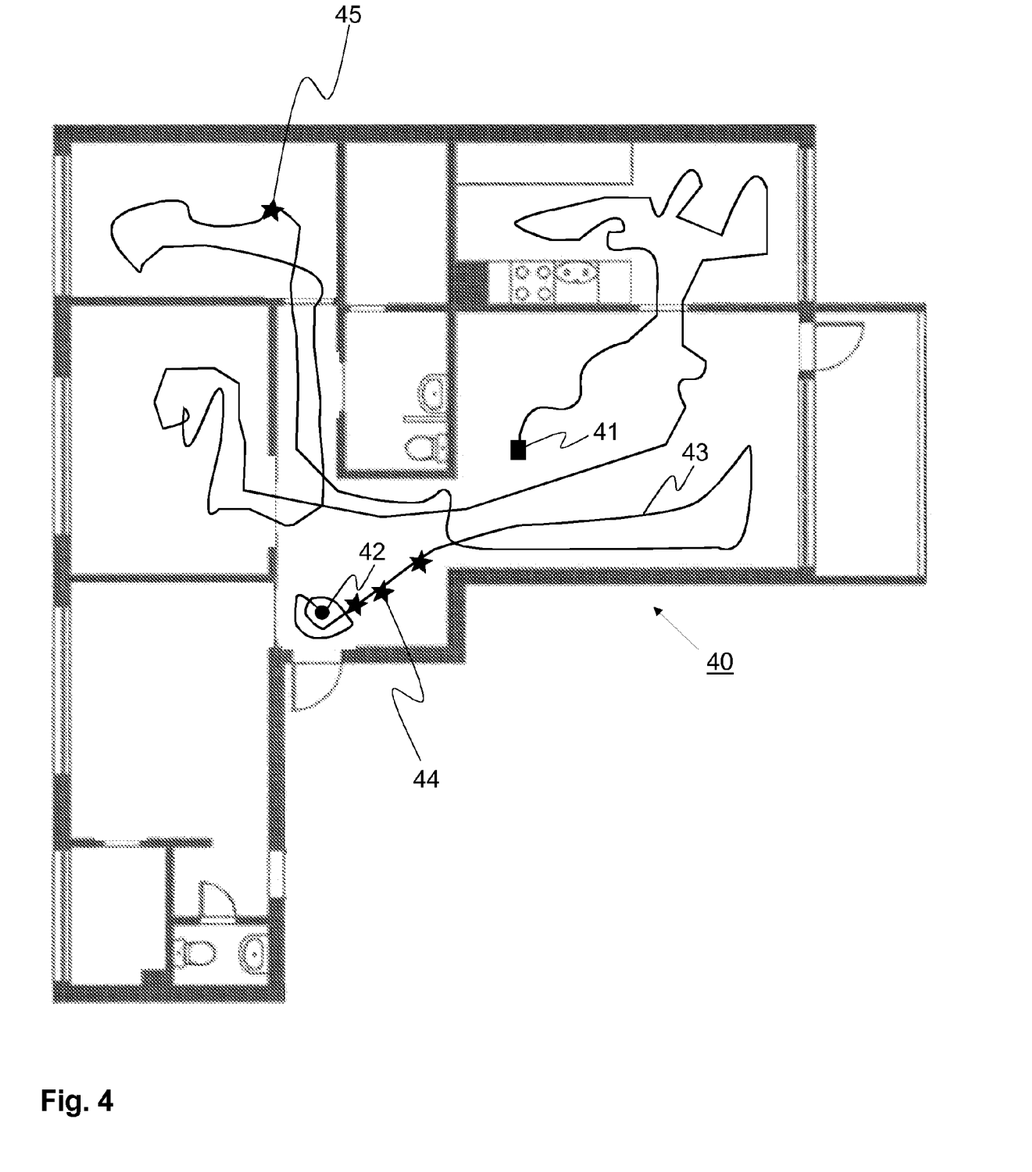
FIG. 4 shows an example of the presentation of the monitoring data on a monitoring person's device.

FIG. 1 shows an example of a monitoring and care environment 10 for a living target 1 according to the invention. The care environment 10 can for example be an apartment used as a residence by the human who is the target or by the owner of the pet who is the target. An example of the apartment 40 is shown in FIG. 4. The exemplary care environment 10 of the target (a dog in the example of FIG. 1) shown in FIG. 1 advantageously includes a wireless monitoring device 2 carried by the target, a base station 13 of a wireless data transfer network with an antenna 13a, a wireless data transfer network 16 and a computer 17. The care environment 10 can advantageously also include one or more RFID readers 14c, IR sensors 14b, video cameras 14a, food dispensers 12a, water dispensers 12b, treat dispensers 12c, animation arrangements 11, a heating, plumbing and air conditioning adjustment arrangement 15a and an environment condition adjustment arrangement 15b.

The target monitoring device 2 according to the invention shown in FIG. 1 is connected via a wireless radio link 18 to at least one base station 13 belonging to the monitoring arrangement 10. The base station 13 can for example be a device, which can be connected to a USB port in a computer. The wireless radio link 18 can for example be an infrared link (IR), a wireless link according to the BLUETOOTH communication standard, a wireless link according to the ZIGBEE communication protocols, a WLAN link or some cellular network link. Because the distance between the monitoring device 2 carried by the target and the base station 13 of the wireless radio network is short, the transmitting power of the monitoring device 2 is also low. This makes possible a long operation time for the monitoring device 2 carried by the target 1, for example the dog.

The monitoring arrangement 10 according to the invention can provide "remote care" or "remote nurture", "virtual interaction with the target" and "a communication contact with the remote target 1". The invention makes possible the presence of the relative or owner with the target 1, such as the elderly human or dog, during the day, without physically going to the target. The presence of the owner or relative can mean many things, such as for example listening to, talking to, petting or playing with the target 1. The presence can be expressed also as expressions, gestures or hand signals, which are achieved with the aid of a suitable animation means 11, such as for example a monitor and web camera.

The presence can also comprise training the dog by giving instructions and rewarding/punishing with the aid of technical means. It can also mean controlling the feeding of the dog with a dispenser 12a and drinking with a water dispenser 12b so that the voice, face or hands 11a of the mistress or master are virtually present, advantageously via an animation arrangement 11.

Said rewarding or punishing means can for example be a part of the monitoring device 2 carried by the dog. The monitoring device 2 can for example have a citric acid sprayer and/or a sprayer with the owner's scent, which are used according to the obedience of the pet 1. For example if the pet according to the monitoring data is in an area, where it is not desired for it to move, the owner can give a citric acid spray as a punishment. If the pet leaves the undesired area, the owner can reward it by giving the pet a spray, which pleases the pet, as a reward. The pet can receive a reward for obeying an order also from a separate treat dispenser 12c.

The monitored pet 1 shown in the example of FIG. 1 can for example be a dog. In the shown exemplary monitoring system 10 the pet 1 is equipped with at least one monitoring device 2 according to the invention. If the pet is a dog, the monitoring device 2 can advantageously be shaped as a collar, which the dog carries at all times when it is alone in the apartment.

The monitoring device 2 at the neck, wrist or clothes of the target advantageously comprises a 3D acceleration sensor. By integrating the measurement data from the acceleration sensor with time, the path of the target in the apartment is discovered over a selected time interval. The data of the acceleration sensor can advantageously also be used to draw a "map" of the apartment with the aid of the movement of the target. The map/floor plan of the apartment can alternatively be created/drawn also so that the owner moves the 3D acceleration sensor in the entire apartment. If there are several targets, such as dogs or humans, each of them advantageously has their own individual monitoring device.

The floor plan of the room can be obtained for example as follows. The monitoring device 2 is brought to the "home place" of the target. At the home place the acceleration measurement is started in the monitoring device 2. Thereafter one moves with the monitoring device 2 in hand from the home place of the target to the corner of the closest room when turning for example clockwise. The monitoring device is held in an essentially horizontal position near the corner (for example about 10 cm from both walls, or if it is an outer corner about 10 cm from the corner). At the corner the position measurement is registered again for example by pressing a button in the monitoring device 2. Thereafter one keeps moving in a clockwise direction to the next corner and acting in the above described manner. In order to obtain a floor plan of the apartment, the entire apartment is circled by following the walls. Each time when turning in a new direction in a slanting or straight angle, the position measurement is registered.

When finally arriving back at the starting point, i.e. at the home place of the target, the monitoring device 2 is deactivated with a suitable function related to the monitoring device 2.

Thereafter the monitoring device 2 is connected to a computer and the therein generated floor plan is accepted. If needed, the image can be edited, for example windows and furniture can be added and the locations of walls and corners can be moved.

The 3D acceleration sensor is an example of a sensor, with which the position of a monitored target, such as a dog or a human, can be determined three-dimensionally. Other positioning technologies can also be utilized in the monitoring system according to the invention. The monitoring device 2 can also contain a compass or a gyro sensor, which can be utilized in determining the movement direction. Examples of other positioning technologies are the RSSI (received signal strength indication) and TOF (time of flight) method known from wireless sensor networks applied to radio waves or ultra sound and positioning based on RFID readers. The position data calculated by the 3D acceleration sensor can be calibrated and specified from time to time for example by means of fixed RFID readers 14c or IR indicators 14b.

The position data of the target can advantageously be calibrated for example with the aid of the sleeping place of the target. The sleeping place and sleeping position are often unchanged from day to day. The target sleeping or resting is indicated by the fact that no new acceleration data is received from the target during a certain time. When the target finally begins to move, the defined sleeping place data and the acceleration measurement data can be used to determine a probable movement direction of the target. If, when starting to move, the dog seems to be walking "through a wall", the monitoring system knows that the co-ordinates of the monitoring device 2 have turned during the sleep or rest of the target. In that case the monitoring system turns or moves the co-ordinates of the floor plan of the apartment so that the path of the target can be fitted into the floor plan of the apartment. Further in such cases, other positioning methods can also be used when the target moves, in order for the position of the target to be determined precisely at a certain time. When the precise positioning has been done once, the acceleration measurement can again be used alone to monitor the movement of the target. Such a monitoring system does not necessarily need measuring of the compass direction at any time.

In the monitoring system according to the invention the movement of the target 1 is monitored and stored and this data is utilized for sending possible alarms. For example the sharp sense of smell of a dog can indicate smoke earlier than a fire alarm. Thus the movement and gesticulation of a dog can give a fire alarm signal much earlier than a fire alarm.

Statistics regarding the target's 1 movement in the apartment can advantageously be compiled for a longer time period. A change in the movement manner can indicate a change in the condition or health problems in the target. From the monitoring system 10 according to the invention it is possible to create a data transfer connection to a doctor or a veterinarian already before the actual patient visit.

The instinctual behaviours of the dog 1 and their changes are the dog's way of telling its owner how it feels. In a normal situation the dog 1 moves between the sleeping place, the feeding place, the front door and windows and the play places. If the route depicting the movement of the dog 1 changes for one reason or another, it can indicate a change in the condition or health problems in the dog 1.

A relative or an owner can monitor the map from for example a computer monitor at his workplace, in which map a map of the apartment and possible garden is seen and therein the path used by the target is marked for example with lines. The travel time can advantageously be coded with different colours or line shapes. For example bright red can illustrate the activity history of the last 15 minutes, yellow the history from 15 to 60 minutes ago, green the history from 1 to 3 hours, etc.

The monitoring system 10 advantageously comprises means with which the path of the target 1 can be analyzed by calculating a correlation for example with the paths of the previous days. The latest path of the target can be compared for example to the average path of the paths of the last ten days. Data used in the comparison can be for example how many hours the target 1 on average stays at the sleeping place, front door, feeding place etc.

In the monitoring arrangement according to the invention the owner of the pet can examine where in the apartment the dog has made sounds, such as barked, and for how long.

The owner or relative can advantageously start up a computer program in a computer 17, which computer program gives an alarm based on movement or sounds of the target, which differ from what is normal.

If the dog for example lingers at the front door longer than a certain time and simultaneously barks more times than a set barking limit, the owner advantageously receives an alarm via SMS or a SKYPE VOIP call is directly opened to him, with which he can go and listen to what is happening in the apartment. If the monitoring arrangement 10 includes for example a web camera 14a, the owner can also see what is happening in the apartment. The owner can further speak to his dog and calm it down, if for example a person lingering behind the door based on the camera image is someone familiar. Or he can warn the person at the door via a loudspeaker, which advantageously belongs to the monitoring arrangement 10. Thus the guarding function of the dog can also be used remotely.

In the monitoring arrangement 10 according to the invention it is possible to adjust, based on the movement of the dog, for example the lighting and temperature of the apartment with the aid of a heating, plumbing and air adjustment device 15a and a condition adjustment device 15b. The adjustments can be performed either as a procedure by the owner via the internet or as an automatic function with the aid of a computer program in the computer 17. If the dog is not moving, the apartment is advantageously dimmed. In connection with the condition adjustment it is possible to play for example calming music or other calming sounds to calm down the dog.

With the aid of the monitoring arrangement according to the invention the owner can via the internet check that the automatism has worked in a desired manner. With the aid of the monitoring arrangement the dog can also be taught to recognize upcoming occurrences with the aid of different pieces of music: Some piece of music which starts softly but soon changes to allegro tells that the owner will soon make contact via the loudspeaker, some other piece of music tells that the owner can soon be seen on the monitor, and a third one tells that the owner will soon be heard and will give food with the aid of the remote feeding device 12a and 12b. This is made to increase the bond with the owner.

With the aid of the monitoring arrangement 10 according to the invention it is possible to train the dog with the aid of taste stimulations. The dog is given a task, the correct performance of which is rewarded with a treat, which comes to the dog along with speech and/or possibly a picture 11a of the owner on the monitor. The picture 11a of the owner can be projected to be visible to the dog. The "owner picture" can control the feeding or give various commands (e.g. NO). The dog's access to water and food can be monitored for example with the aid of RFID sensors 14c at the feeding place. The dog can be given a reward also with the aid of a sort of scratching device. The owner can via the internet control the scratching device to be active, if the dog has behaved according to the given commands. The owner's voice or picture is advantageously connected with this scratching occurrence.

With the aid of the monitoring arrangement according to the invention it is possible to teach the dog to use either an "inside bathroom" or to command the dog to the garden to do its business, if such a thing should become necessary. The back door of the apartment thus advantageously has a hatch, from which the dog can get into the garden to do its business and to exercise. The hatch in the back door advantageously locks itself when the dog has returned from the garden back into the apartment or moves in the garden at a distance from the hatch. The outside turf or allowed staying area for the dog can also be determined based on the measurement data from the 3D acceleration sensor in the monitoring device 2 according to the invention. If the dog leaves the allowed area in the outside area, this is "punished", if necessary.

In an embodiment of the invention the dog 1 is equipped with several different monitoring devices. A 3D monitoring device 2 monitors the dog's movement and a second monitoring device (not shown in FIG. 1) makes it possible to monitor for example how the dog whips its tail and/or its vital functions, such as body temperature and heart rate.

Figure 2:
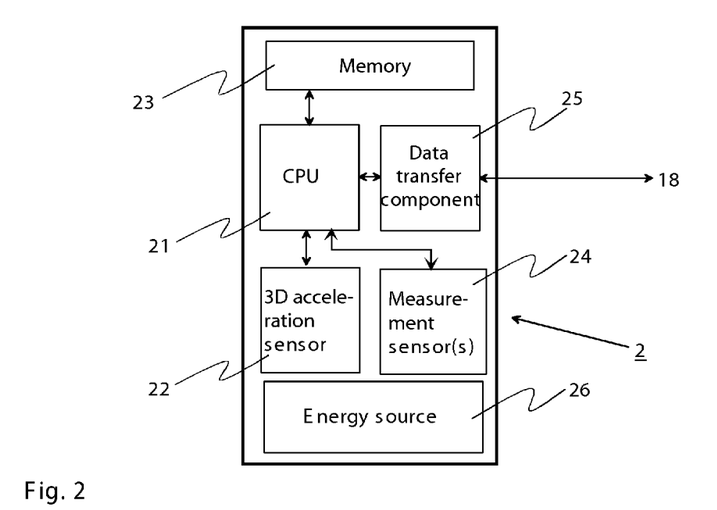
FIG. 2 shows an advantageous embodiment of a monitoring device carried by the target.

FIG. 2 shows an advantageous embodiment of a monitoring device 2 carried by the target. The monitoring device 2 advantageously comprises an energy source 26, such as a battery or an accumulator. The energy source 26 can advantageously be charged for example by connecting it to a USB port in the computer. The electric components in the monitoring device 2 get the energy they need for their function from this energy source 26. There is at least one 3D acceleration sensor 22 in the monitoring device 2. The measuring area of the 3D acceleration sensor is advantageously ±10 g.

The measurement data from the 3D acceleration sensor 22 is processed in the measuring event in the processing unit 21 (CPU, Central Processing Unit) of the monitoring device 2. The processing unit 21 is connected to a memory 23. The memory 23 is used for storing the computer programs needed in the processing of measurement values according to the invention. All the variable values measured with the monitoring device 2 are also stored at least temporarily in the memory 23. Results calculated from the measured variables are also stored in the memory 23.

An example of the calculation of a variable performed by the processing unit 21 is the calculation of the position data using measured acceleration data. The position calculation program according to the invention is stored in the memory 23. The computer program comprises computer program commands, by using which the processing unit 21 calculates from the 3D acceleration measurement data the displacement of the monitoring device 2 in three dimensions between two consecutive acceleration measurements.

The processing unit 21 is connected also to a data transfer component 25. With the aid of this data transfer component a data transfer connection is formed to a base station 13 of a wireless data transfer network belonging to the monitoring system. The data transfer component 25 advantageously supports at least one data transfer method. Some advantageous methods usable in data transfers are infra red technology (IR), BLUETOOTH wireless standard technology, ZIGBEE communication protocol technology, WLAN technology and various time or code division data transfer technologies used in cellular networks. Measurement data stored in the memory 23 of the monitoring device 2 via the data transfer component are transferred via the wireless data transfer connection 18 to the base station 13. From the base station the measurement data is transferred via the data transfer connection 16 to the computer 17 to be stored. The data transfer connection 16 can be either a wireless connection or a cable connection or a combination thereof.

The data transfer component 25 advantageously also comprises data transfer means, which can communicate with a RFID reader. By using data from the RFID reader 14c, the position data of the monitoring device 2 calculated from the data of the 3D acceleration sensor can be confirmed in the computer 17 for example in a situation, where the monitored target seems to be passing "through a wall". When needed, the position data calculated from the acceleration measurement data is advantageously corrected to correspond to the position data received from the RFID reader.

The monitoring device 2 can advantageously comprise also other measurement sensors 24 than the 3D acceleration sensor 22. Examples of other types of sensors are a compass, a gyro sensor, a bark sensor, a sensor measuring the body temperature and a sensor monitoring the heart rate. The processing unit 21 processes the data also from these measurement sensors and stores it at least temporarily in the memory 23. In connection with the storing the processing unit 21 combines the data from other measurement sensors with the position data received from the acceleration sensor. The combined measurement data are stored in the memory 23, from where they are transferred at times to the computer 17 for further processing.

When the target starts to move from the rest place it is possible that the co-ordinates of the monitoring device 2 have rotated during the time the target has laid down. Due to the rotation of the co-ordinates it may seem like the target is moving "through a wall". In such a case the measurement data from a compass or a gyro sensor can in an embodiment of the invention be used in determining the movement direction of the dog when the target goes from resting or laying down to moving. From these measurement data the real direction the dog starts to move in can be discovered, with which direction the direction data given by the acceleration measurement is advantageously corrected.

In another embodiment of the invention the known home place and sleeping position of the target can be used also in calibrating the co-ordinates of the monitoring device 2. If the monitored target mostly sleeps in the same position/direction, the monitoring system advantageously updates/calibrates the co-ordinates of the sleeping place from this still staying data.

In an advantageous embodiment of the invention the monitoring system learns to make standard corrections automatically after it has done the same "walking through a wall" correction already a few times and noticed that the "walking through walls" stops with said corrections of the co-ordinates.

Figure 3:
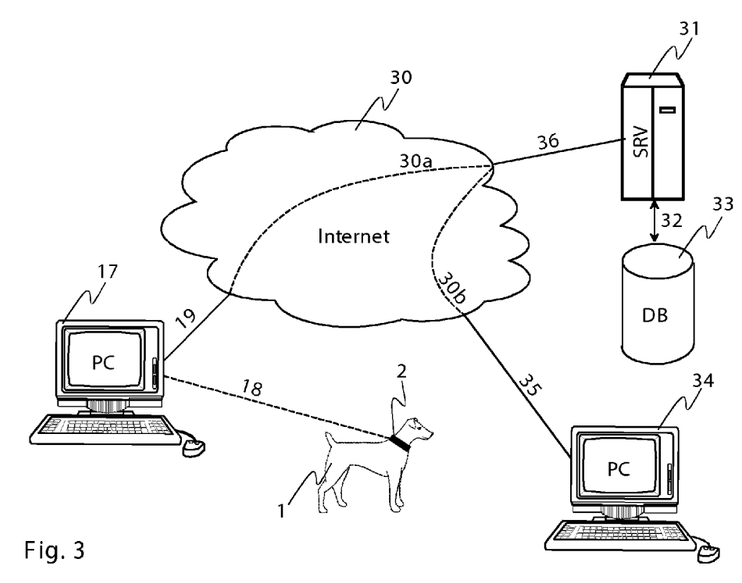
FIG. 3 shows an advantageous embodiment of a data transfer arrangement used in the monitoring of the target.

FIG. 3 shows an example of using the monitoring data in an internet environment, when the monitored target is a dog. The pet 1 has a monitoring device 2, which continuously measures at least the whereabouts of the pet. The measured monitoring data is transferred through a data transfer network 18 to a computer 17 in the owner's possession. The measurement data is stored in the computer 17 at least temporarily.

A data transfer connection 19 can be created from the computer 17 to the internet 30. The server 31, which is advantageously used for utilizing the monitoring data, is also connected via a data transfer connection 36 to the internet. A data transfer connection 30a can thus be created via the internet between the computer 17 and the server 31. This arrangement makes possible the transfer of the measurement data received from the monitoring device 2 from the computer 17 to the server 31 for further analysis and possible presentation. The transferred measurement data from the monitoring device is stored in a database 33 via the data transfer connection 32.

Reference number 34 shows a second data processing device, which is able to create a data transfer connection 35 to the internet 30. Via the data transfer connection 30b created to the internet, an analysis and presentation request for data regarding the monitoring device 2 can be made from the data processing device 34 to the server 31. The server 31 checks if the service request made by the data processing device 34 is allowed or not. If the service request is allowed, the server 31 retrieves the data of the monitoring device 2 defined in the service request from the database 33 for the time period defined in the service request. The server 31 processes the measurement data and sends the processed data to the data processing device 34. The data processing device 34 can either be a data processing device used by a relative or an owner or a data processing device in the possession of some third party, to whom the relative or the pet 1 owner has granted right to monitor the pet's 1 situation.

The monitoring arrangement shown in FIG. 3 makes it possible to provide via the internet activity data regarding a relative or a pet to all willing parties. The system also makes possible the creating of a kind of remote dog care facility. If the data processing device 34 can be used to monitor the activity of several owners' dogs at the same time, it makes possible the physical care procedures of the dogs always at the right time. If the monitoring data of some dog 2 shows that the dog must be visited for one reason or another, the person performing the monitoring can go straight to the problematic care animal. Thus the problem can quickly be fixed.

The behaviour of dogs can predict a coming natural disaster. Thus if the arrangement according to FIG. 3 is used to monitor a large group of dogs, a simultaneous change in behaviour in several dogs can be used to predict a coming catastrophe, for example a gas leak, an earthquake, a volcanic eruption or a tsunami.

The server/terminal architecture according to FIG. 3 makes possible the creating of a virtual community service. For example compiling statistics of and comparing the activity modes of different individuals of a certain dog breed in order to analyze the care practices or state of health becomes possible for example within breed associations.

The dog owners who have joined the community service can also exchange information relating to the care and condition of their dogs with each other or for example arrange competitions between dogs, using the measurement data collected from the pets. Checking different alarms caused by the behaviour of a dog can also be handled with the aid of people, who have joined the community service. For example if the behaviour of the dog points to a burglar, a member of the community service, who lives nearest and is present, can go and check if it is a burglar or not. If needed, the person who has done the checking can inform the owner and/or the authorities.

FIG. 4 shows an example of a pattern illustrating the movement of a dog presented in the monitoring system according to the invention. The floor plan of the apartment 40 is created with some graphic drawing program according to prior art. For example by moving the monitoring device 2 on the dog in the apartment 40, the dimensions of the floor plan can with the measurement sensor be calibrated into the measurement data of the monitoring device.

In the example in FIG. 4 the monitoring of the dog has started in point 41. The line 43 illustrates the movement of the dog in the apartment 40 during the time period selected as the monitoring period. The line 43 is advantageously modified in a way by which the movement of the dog at different times can be presented. The movement time can for example advantageously be coded with different colours or line shapes. For example bright red can illustrate the activity history of the last 15 minutes, yellow the history from 15 to 60 minutes ago, green the history from 1 to 3 hours, etc. By using a coding procedure, a clear picture of the dog's movements at different times is obtained.

Reference number 42 illustrates the position of the latest measurement. Reference number 44 can be used to illustrate for example the places, where the dog has for some reason or other barked or otherwise made sounds. Reference number 45 illustrates the place, where the dog has rested. If the measured rest place 45 is the usual place for the dog in question, the known rest place 45 can be used to calibrate the measurement data depicting the movement of the dog coming from the 3D acceleration sensor, when the dog starts to move after its rest. Thus a measurement error caused by a possible turning of the measurement directions of the 3D sensor, which has happened during the rest, is avoided.

From the path graphs 43 one can for example with one glance see if the dog has moved in the apartment in rooms, where it should not move. If this has happened, the owner can immediately intervene in the movement of the dog by using remote training means.

A corresponding path graph is obtained also in a situation, where the monitoring device 2 is on a human, who is the target of the monitoring.

Figure 5:
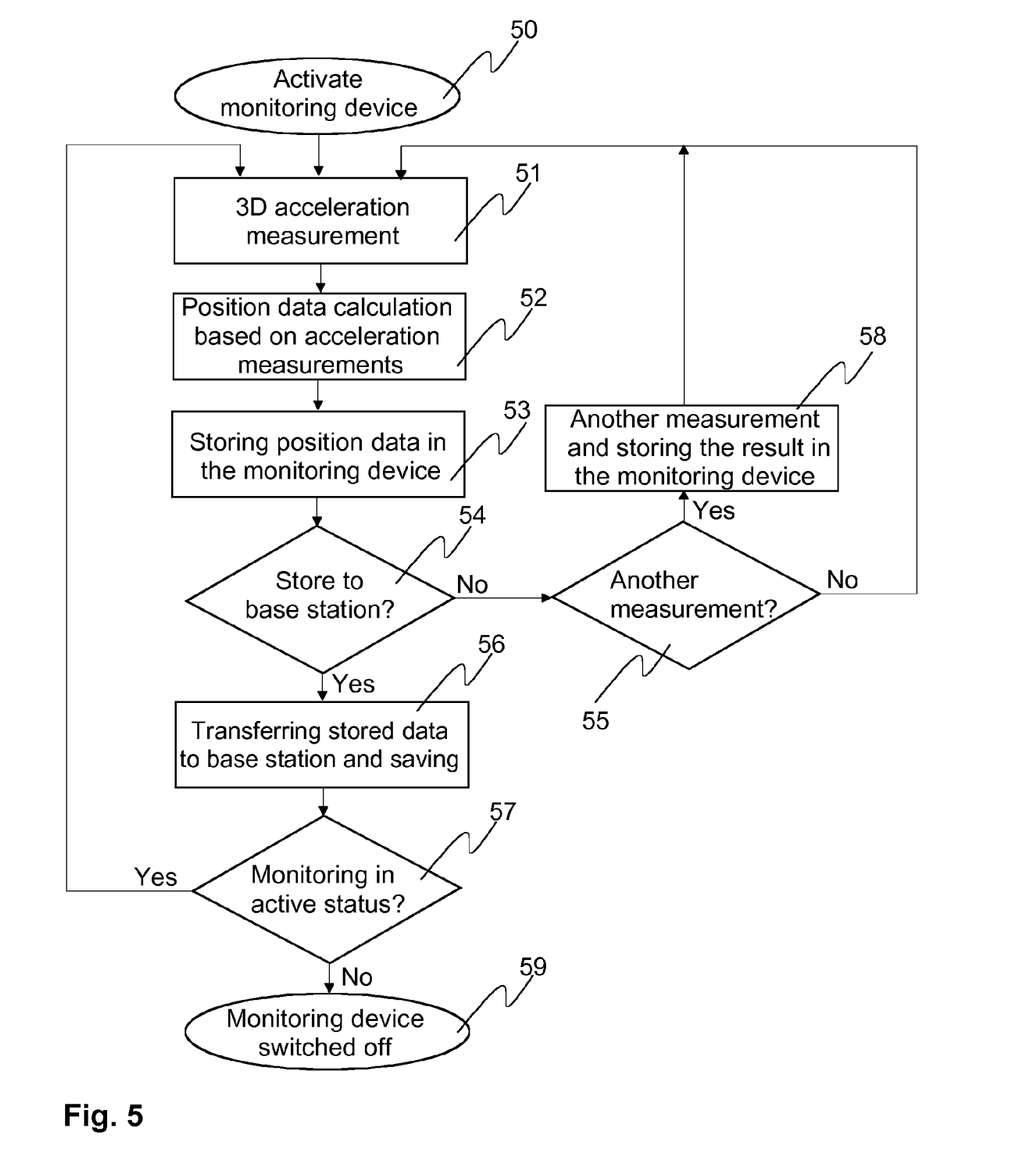
FIG. 5 shows as an exemplary flow chart the main functions performed by the device carried by the target in the monitoring method according to the invention.

FIG. 5 shows as an exemplary flow chart the main functions performed by a monitoring device 2 during the monitoring of a dog 1 or a human. In step 50 the monitoring device 2 is activated. The monitoring device 2 can be activated for example by switching on power in the monitoring device 2 from a power switch in the monitoring device. As a result of the activation of the monitoring device 2 at least the 3D acceleration measurement starts 51 in the monitoring device. In connection with the activation the position of the monitoring device 2 in the used floor plan co-ordinates of the apartment is advantageously calibrated. Thereafter the monitoring device 2 continuously measures the accelerations in three mutually perpendicular dimensions.

In step 52 the processing unit 21 of the monitoring device 2 calculates, with two successive acceleration measurements, how much and in which direction the monitoring device 2 has moved between these measurements. In step 53 the calculated position data is stored in the memory 23 of the monitoring device 2.

In step 54 a checking is performed to determine if the stored measurement data is transferred via the base station 13 to the computer 17. If it is in step 54 found that no storing is done at this time, the process moves to step 55, where a checking is performed to determine if some other measurement regarding the dog or human should be performed. If it is in step 55 found that no other measurements will be performed, the process returns to step 51, whereafter a new acceleration measurement is performed.

If it is in step 55 found that other measurements than the acceleration measurement will be done, the process moves to step 58. In step 58 the other specified measurements are performed and their results are stored in the memory 23 of the monitoring device 2. In connection with the storing a temporary link is created between the measured other measurement data and the closest acceleration measurement data. By proceeding in this manner, the calculated position data and other measurement data can be presented temporally in the correct time ratios later. After the storing the monitoring process returns to step 51, where a new acceleration measurement is performed.

If it is in step 54 found that the measurement data stored in the memory 23 of the monitoring device 2 is transferred to the computer 17, the process branches out into step 56. The data transfer can be started for example at certain time intervals, when the storing capacity of the memory 23 is filled up or by a command coming from the computer 17. In step 56 the measurement data stored in the memory 23 of the monitoring device 2 is transferred via the base station 13 of the monitoring arrangement to the computer 17.

After the performed data transfer, a checking is performed in step 57 to determine if the monitoring is still in an active state or not. If the monitoring is still in the active state, the process returns to step 51, where a new acceleration measurement is performed.

If it is in step 57 found that monitoring of the dog or human does not need to be done anymore, the monitoring device 2 is switched off in step 59. The switching off can advantageously be done with a command sent by the computer 17 to the monitoring device 2. The received switch-off command is advantageously performed after the first data transfer 56, which comes into turn to be performed after the switch-off command for the monitoring sent by the computer 17.

Figure 6:
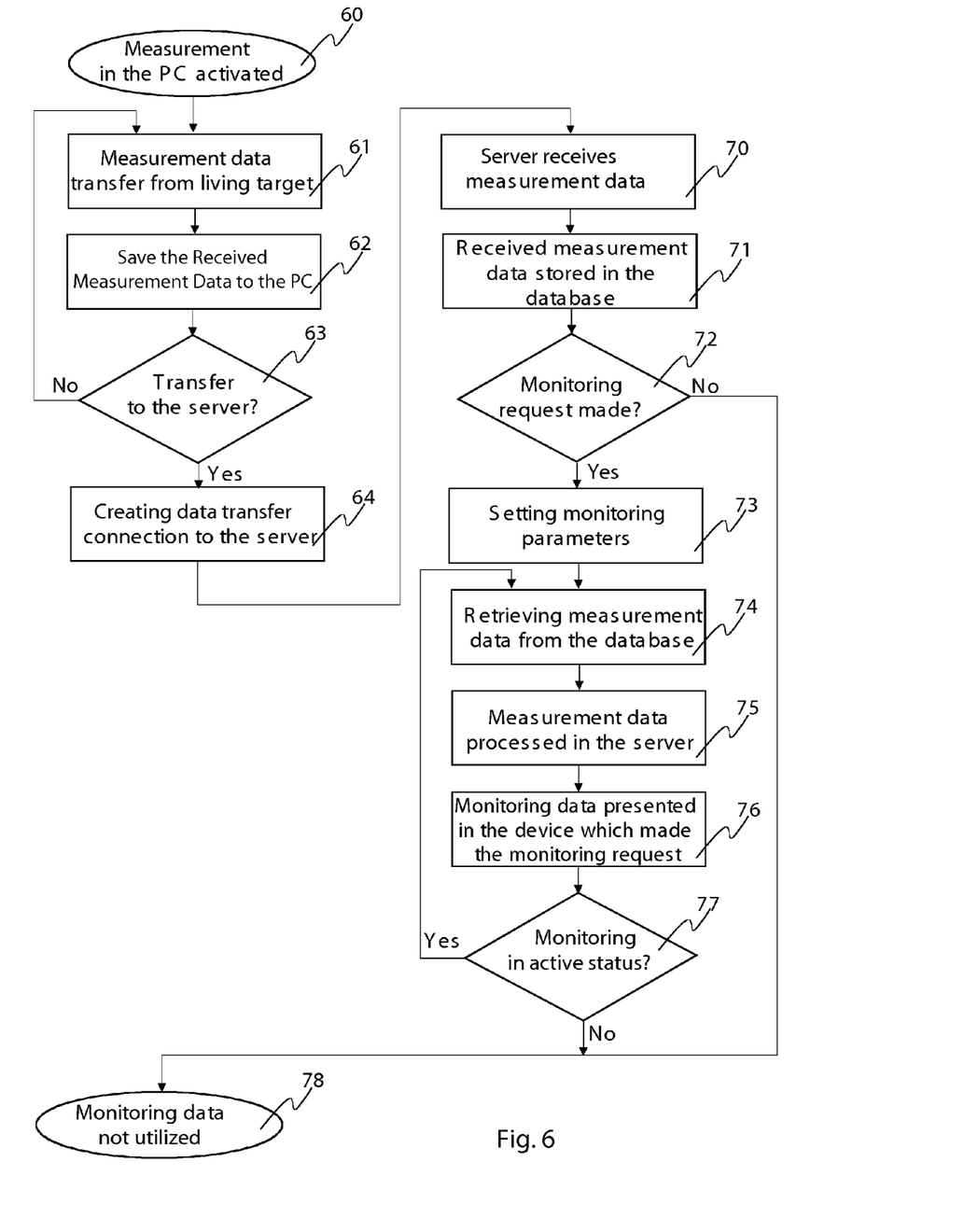
FIG. 6 shows as an exemplary flow chart the main steps used in the presentation of the monitoring data of the target and FIG. 7 shows as an exemplary flow chart how data describing the path is calibrated using the defined rest place.

FIG. 6 shows as an exemplary flow chart the main steps in the monitoring process of the computer 17 and server 31. In step 60 the monitoring program in the computer 17 is activated. In the active state the computer 17 can receive and send information either from/to the server 31 or from/to the monitoring device 2.

In step 61 the measurement data in the memory 23 of the monitoring device 2 is transferred to the computer 17. The data transfer can be started either by the computer 17 or the monitoring device 2.

In step 62 the measurement data received from the monitoring device 2 is stored in the memory of the computer. When the received measurement data is stored, a checking is performed in step 63 to determine if the stored measurement data is transferred to the server 31 or not. If the checking 63 gives the result that the measurement data is at this step not transferred to the server 31, the computer returns to step 61 to await the next transfer of measurement data from the monitoring device 2 on the target, such as for example the dog.

If the checking in step 63 gives the result that a transfer of measurement data to the server 31 should be performed, then in step 64 the computer 17 creates a data transfer connection via the internet to the server 31.

In step 70 the computer 17 sends the measurement data stored last to the server 31, which receives the measurement data. In step 71 the server 31 stores the measurement data in a database 33. Thereafter a checking is advantageously performed in the server to determine if there is a monitoring request regarding the stored measurement data. If no monitoring request has been made, the server process moves to step 78, where the stored measurement data is not processed for presentation.

If it is in step 72 found that at least one monitoring request has been made regarding the monitoring device 2, from which the measurement data was received, the process moves to step 73. In step 73 the monitoring parameters are checked or set. Examples of the monitoring parameters are monitoring time interval, position data, barking, body temperature and heart rate.

In step 74 the server retrieves the measurement data regarding the selected monitoring device 2 and the selected monitoring parameters from the database 33. In step 75 the server 31 processes the measurement data with a suitable computer program so that information regarding the selected parameters is discovered from the measurement data. If needed, a position and direction calibration is performed on the measurement data based on the last verified rest place, before the measurement data is sent to the data processing device 34.

In step 76 the processed monitoring data is sent via the internet to the data processing device, which has made the accepted monitoring request. The processed monitoring data is transferred in ready presentation format to the data processing device 34, which made the monitoring request.

When the processing and presentation of the data has been made, a checking is next performed in step 77 to determine if some monitoring request regarding the monitoring device 2 is still in force. If there is no unanswered monitoring request left, the process moves to step 78, where the measurement data in the database 33 is not at that moment utilized.

Figure 7:
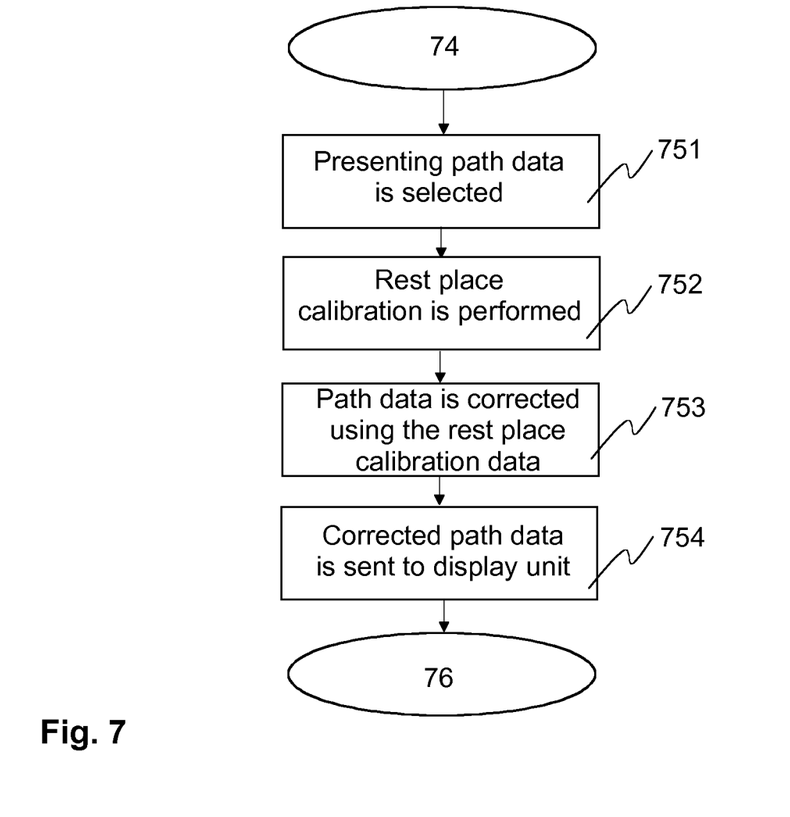

In FIG. 7 is shown as an exemplary flow chart the main software functions performed by the server in step 75 in FIG. 6 in a situation, where rest place and direction calibration is performed before the measurement data related to the path of the target is sent.

In step 751 the monitoring of the path of the target in the apartment is selected as the monitoring parameter.

In step 752 the rest place calibration is performed with the aid of the last verified rest place. In the rest place calibration the earlier measured rest place position data and the data depicting the stored average direction of movement after rest are retrieved from the monitoring database.

In step 753 the monitoring data measured after the rest is corrected using the rest place calibration data. With the aid of the rest place calibration the measurement directions and the measurement starting place for the 3D acceleration sensor can be determined for the monitoring so that the presented path corresponds to the actual movement of the target in the apartment.

In step 754 the path data corrected with the rest place data is sent to the monitoring person's device.

In step 76 the path corrected with the rest place data is presented on the monitor of the monitoring person's device.

All the process steps of the monitoring of the activity of the target shown in FIGS. 5 to 7 can be realized with computer program commands, which are performed in a suitable general-purpose processor or special-purpose processor. The computer program commands can be stored in a computer-readable media, such as a data disk or a memory, from where the processor can retrieve said computer program commands and execute them. The references to computer-readable media can for example also contain special components, such as programmable USB Flash memories, logic arrays (FPLA), application-specific integrated circuits (ASIC) and signal processors (DSP).

Some advantageous embodiments of the method and device according to the invention have been described above. The invention is not limited to the solutions described above, but the inventive idea can be applied in numerous ways within the scope of the claims.

We claim:

1. A method for presenting a path of a living target via a data transfer network, the method comprising:
    measuring continuously, with a wireless monitoring device in real-time, 3D acceleration data caused by a movement of a living target,
    storing 3D acceleration data defined with the wireless monitoring device into a database accessible via a data transfer network, and
    editing from the 3D acceleration data stored in the database an illustration of the path of the living target, which illustration can be presented via a data transfer network, which illustration is presented on a monitor of a data processing device, wherein in order to present the path of the living target, the method comprises:

performing calibration of a sleeping place of the living target which is unchanged from day to day, according to a path history of the living target, correcting with the sleeping place, a measurement location data and a measurement direction data related to a short-term of the 3D acceleration measurement data, wherein the short-term of the 3D acceleration measurement data comprises at most a previous three hours, starting from the sleeping place, and sending corrected path data to at least one data processing device, wherein performing calibration of the sleeping place of the living target comprises deriving coordinates of the sleeping place from still staying data of the measured real-time 3D acceleration data, and the measurement location data and the measurement direction data are further corrected with the aid of the sleeping place.

2. The method according to claim 1, further comprising:

storing long-term average sleeping place measurement data for the living target wherein the long-term average sleeping place measurement data comprises sleeping place measurement data from at least a previous three days; and using the long-term average sleeping place measurement data in performing the calibration of a sleeping place of the living target.

3. The method according to claim 2, wherein performing calibration of a sleeping place of the living target further utilizes RFID reader data.

4. A monitoring arrangement for a path of a living target, the monitoring arrangement comprising:

an at least partly wireless data transfer network, a wireless monitoring device, which comprises determining 3D acceleration sensor and a CPU configured to determine a position change of a living target in real-time with 3D acceleration measurement data and a data transfer connection to the wireless data transfer network, a storing computer connected to the wireless data network configured to store the 3D acceleration measurement data of the living target in a database accessible via the wireless data transfer network, and a server configured to:

edit the 3D acceleration measurement data stored in the database into an illustration presenting a path of the living target, which illustration can be presented via the wireless data transfer network, which illustration is arranged to be presented on a monitor of a data processing device;

determine and calibrate sleeping place data of the living target, which is unchanged from day to day, according to a path history of the living target in question;

correct, with the sleeping place data, measurement location data and measurement direction data related to a short-term of the 3D acceleration measurement data, wherein the short-term of the 3D acceleration measurement data comprises at most a previous three hours, starting from a latest sleeping place; and send corrected path data to at least one data processing device, wherein the server derives coordinates of the sleeping place wherein performing calibration of the sleeping place of the living target comprises deriving coordinates of the sleeping place from still staying data of the measured real-time 3D acceleration data, and the measurement location data and the measurement direction data are further corrected with the aid of the sleeping place.

5. The monitoring arrangement according to claim 4, wherein long-term average sleeping place measurement data for the target, is stored in the database, wherein the long-term average sleeping place measurement data comprises sleeping place data from at least a previous three days, and the long-term average sleeping place measurement data is used to calibrate the sleeping place data of the living target.

6. The monitoring arrangement according to claim 5, wherein calibration of the sleeping place data further uses RFID reader data.

7. The monitoring arrangement according to claim 4, wherein the living target is a human.

8. The monitoring arrangement according to claim 4, wherein the living target is an animal.

9. A server, communicatively connected to a computer readable storage programed with computer readable code that when executed by the server, causes the server to operate to:

receive continuously real-time 3D acceleration measurement data from a monitoring device of a living target, store the received real-time 3D acceleration measurement data into a database, edit the received real-time 3D acceleration measurement data stored in the database into an illustration of the path of the living target, which illustration can be presented via a data transfer network, which illustration is configured to be presented on a monitor of a data processing device, determine and calibrate sleeping place data of the living target which sleeping place is unchanged from day to day according to a path history of the living target, correct, with an aid of the sleeping place data of the living target, the measurement location data and measurement direction data related to a short-term of the real-time 3D acceleration measurement data wherein the short-term of the real-time 3D acceleration measurement data comprise at most a previous three hours, starting from a latest sleeping place of the living target, and send corrected path data to at least one data processing device, wherein the server derives coordinates of the sleeping place wherein performing calibration of the sleeping place of the living target comprises deriving coordinates of the sleeping place from still staying data of the measured real-time 3D acceleration data, and the measurement location data and the measurement direction data are further corrected with the aid of the sleeping place.

10. The server according to claim 9, wherein long-term average sleeping place measurement data of three to ten days for the living target, which data is included in the database, is configured to be used to calibrate the sleeping place data of the living target.

11. The server according to claim 10, wherein the calibration of the sleeping place data is further configured to utilize RFID reader data.

12. The server according to claim 9, wherein the living target is a human.

13. The server according to claim 9, wherein the living target is an animal.

14. A computer product, comprising a computer program code stored on a non-transitory computer-readable storage, which computer program code is configured to perform when said computer program code is run on a computer:

Measuring continuously with a wireless monitoring device in real-time 3D acceleration data caused by the movement of a living target, storing the measured real-time 3D acceleration data defined with the wireless monitoring device into a database accessible via a data transfer network, editing from the real-time 3D acceleration data stored in the database an illustration of a path of the living target, which illustration can be presented via a data transfer network, which illustration is presented on a monitor of a data processing device, performing calibration of a sleeping place of the living target, which sleeping place is unchanged from day to day according to a path history of the living target, by utilizing a long-term average sleeping place measurement data of three to ten days, correcting with an aid of the long-term average sleeping place measurement data a measurement location data and a measurement direction data related to short-term 3D acceleration measurement data, the short-term 3D acceleration measurement data comprising at most 3D acceleration data from a previous three hours, starting from a latest sleeping place, and sending corrected path data to at least one data processing device, wherein performing calibration of the sleeping place of the living target comprises deriving coordinates of the sleeping place from still staying data of the measured real-time 3D acceleration data, and the measurement location data and the measurement direction data are further corrected with the aid of the sleeping place.

15. The computer product of claim 14 wherein correcting measurement direction data comprises deriving a real direction from at least the sleeping place, compass measurement data, and a floor plan of a care environment.

* * * * *